United States Patent [19]

Becker et al.

[11] Patent Number: 4,931,428
[45] Date of Patent: Jun. 5, 1990

[54] 1-TERT-BUTOXY-ω-ALKENES AND THEIR USE AS SCENTS

[75] Inventors: Rainer Becker, Bad Durkheim; Heinz Eckhardt, Ludwigshafen; Manfred Eggersdorfer, Frankenthal; Gerhard Schindler, Mannheim; Klaas Jansen, Ludwigshafen, all of Fed. Rep. of Germany

[73] Assignee: BASF Aktiengesellschaft, Ludwigshafen, Fed. Rep. of Germany

[21] Appl. No.: 338,182

[22] Filed: Apr. 14, 1989

[30] Foreign Application Priority Data

May 4, 1988 [DE] Fed. Rep. of Germany ....... 3815044

[51] Int. Cl.$^5$ ................................. A61K 7/46
[52] U.S. Cl. ...................... 512/25; 568/687
[58] Field of Search .............. 568/687, 689, 693; 512/25

[56] References Cited

U.S. PATENT DOCUMENTS 3,845,108 10/1974 Roelofs et al. ............... 568/812
4,261,839 4/1981 Kleber et al. ................ 568/687
4,814,322 3/1989 Exner et al. ................. 512/25

FOREIGN PATENT DOCUMENTS 2336980 7/1973 Fed. Rep. of Germany ...... 568/687
3510568 9/1986 Fed. Rep. of Germany .
2098609A 11/1982 United Kingdom .

OTHER PUBLICATIONS

Ishikawa et al, Chem. Abst., vol. 87, #135,063Q (1977).
Gardette et al, Tetrahedron, vol. 41, #24, pp. 5887–5899 (1985).
Methoden der Organishen Chemie (Houben-Weyl) Band V11/2a, 1973, pp. 907–927.

Primary Examiner—James H. Reamer
Attorney, Agent, or Firm—Oblon, Spivak, McClelland, Maier & Neustadt

[57] ABSTRACT 1-tert-Butoxy-ω-alkenes of the general formula I

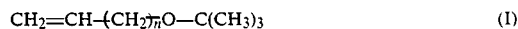

$$CH_2=CH-(CH_2)_n-O-C(CH_3)_3 \qquad (I)$$

wherein n is an integer from 4 to 10, their preparation and their use for imparting fragrance properties to perfumes or to products to be perfumed, or for improving or modifying the fragrance properties of the said perfumes or products, and scent compositions containing these compounds.

5 Claims, No Drawings

1-TERT-BUTOXY-ω-ALKENES AND THEIR USE AS SCENTS

The present invention relates to 1-tert-butoxy-ω-alkenes of the general formula I

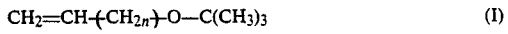

$$CH_2=CH-(CH_{2n})-O-C(CH_3)_3 \qquad (I)$$

where n is an integer from 4 to 10, to their use as scents, i.e. for imparting fragrance properties to perfumes or to products to be perfumed, or for improving or modifying the fragrance properties of the said perfumes or products, and to scent compositions containing 1-tert-butoxy-ω-alkenes of the formula I.

Because of the general shortage of many natural scent components, the necessary adaptation to changing fashion trends and the constantly increasing demand for odor improvers for products in daily use, such as cleaners, cosmetics, glues, etc., the scent industry continuously needs new scents which, alone or in the form of compositions, constitute useful perfumes or fragrance materials having interesting fragrance notes. Since little is known about the relationships between structure and scent properties and controlled synthesis of scents having the desired olfactory properties is therefore impossible, it is necessary to find compounds which possess useful qualities as scents.

It is an object of the present invention to provide novel interesting scents which can be prepared in a very simple manner from readily available and hence cheap starting materials.

ω-Alkenols, such as ω-nonenol (Arctander No. 2357; cf. S. Arctander, Perfume and Flavor Chemicals, Mont Clair, N.Y., 1969) or ω-decenol (Arctander No. 844), have more or less pronounced floral notes, which are reminiscent of rose in the case of decenol. ω-Decenyl acetate (Arctander No. 846) and ω-decenyl propionate (Arctander No. 847) likewise have interesting floral notes but have the considerable disadvantage that they are very unstable toward alkalis. Although ω-hexenyl methyl ether (Arctander No. 2054) is stable to alkalis, it has the disadvantage of being very readily volatile and, according to the stated publication, is very difficult to obtain.

We have found that this object is achieved and that, surprisingly, the novel 1-tert-butoxy-ω-alkenes of the formula I not only have advantageous scent properties but also exhibit good adhesion and stability to alkalis.

For example, 1-tert-butoxyhex-5-ene has a very intense green and herbaceous fragrance with a floral note which is reminiscent of tagetes and is clearly evident in perfume compositions even in low doses. It is precisely this particularly floral effect which makes the compound an interesting scent. Because of its volatility, it is suitable for modifying the top note of perfume compositions. This compound is particularly effective in fresh herbaceous perfume types, doses of from 6 to 8% by weight being possible. In floral compositions, such as carnation and honeysuckle, as well as lily-of-the-valley and rose, as little as from 1 to 3% has a substantial effect.

For example, 1-tert-butoxyhex-5-ene is furthermore important as an intermediate for a technically simple process for the preparation of E-7,Z-9-dodecadienyl acetate, the pheromone of the grape berry moth, Lobesia botrana, which is of interest for controlling these insects by the confusion method. This pheromone was first described in 1973 (cf. U.S. Pat. No. 3,845,108), but the preparation processes known to date are technically very involved.

In contrast, a technically relatively simple method starts from the novel 1-tert-butoxyhex-5-ene. In this procedure, this compound is converted in the presence of a rhodium-triphenylphosphine complex into 7-tert-butoxyheptanal, from which 3-hydroxy-9-tert-butoxy-1-nonyne can be obtained by base-catalyzed reaction with acetylene in an aprotic organic solvent. When subjected to a Meyer-Schuster rearrangement reaction (cf. Houben-Weyl, Methoden der Organischen Chemie, Vol. VII/2 (1973), pages 907–927), 3-hydroxy-9-tert-butoxy-1-nonyne gives 9-tert-butoxy-2-nonen-1-al, the use of which for the synthesis of the desired pheromone active ingredient presents no problems and is described in GB-A-2 098 609 and Liebigs Ann. Chem. No. 2 (1981), pages 1705–1720.

The present invention furthermore relates to a process for the preparation of the novel 1-tert-butoxy-ω-alkenes, wherein the corresponding ω-alkenol of the general formula II

$$CH_2=CH-(CH_{2n})-OH \qquad (II)$$

is reacted with isobutene in the presence of an acidic catalyst.

The ω-alkenols of the formula II are known compounds which can be prepared in high selectivity and purity in a simple manner, for example by partial dehydration of an α,ω-diol (cf. DE No. 35 10 568). Preferred alkenols of the formula II are hexenol, octenol, nonenol, decenol and dodecenol.

The reaction temperature for the tert-butylation may be from 0° to 100° C., preferably from 20° to 50° C.

The reaction can be carried out either in the absence of a solvent or in an inert aprotic organic solvent. Suitable solvents are hydrocarbons, such as hexane, heptane, octane or cyclohexane, or mixtures of these, and ethers, such as methyl tert-butyl ether or tetrahydrofuran.

Suitable acidic catalysts are inorganic acids, such as sulfuric acid, phosphoric acid or hydrochloric acid, and organic acids, such as acetic acid, oxalic acid or p-toluenesulfonic acid, as well as acidic ion exchangers. The process can be carried out under atmospheric pressure or under pressures of from 1 to 10 bar.

Since the tert-butylation is a conventional process, further information is unnecessary.

The novel 1-tert-butoxy-ω-alkenes are interesting scents and useful intermediates for a novel advantageous synthesis route for E-7,Z-9-dodecadienyl acetate, the pheromone of the grape berry moth, Lobesia botrana. They can be prepared in a simple manner from readily available starting materials.

EXAMPLE 1

200 g of hex-5-en-1-ol were dissolved in 250 ml of methyl tert-butyl ether, and 100 g of an acidic ion exchanger (SPC 118 from Bayer in the H+ form) were added. Thereafter, isobutylene was passed into the resulting suspension until the latter was saturated, and the progress of the reaction was monitored by thin layer chromatography. After 4 hours, all the hex-5-en-1-ol had been converted. Fractional distillation of the reaction mixture gave 234 g of 1-tert-butoxy-5-ene of boiling point 66°–67° C./32 mbar. The purity of the product was determined as 98.5% by gas chromatography; the yield was 75% of theory. The compound has a very intense green and herbaceous fragrance with a floral note reminiscent of tagetes.

EXAMPLES 2-4

By reacting 2 moles of alkenol in methyl tert-butyl ether with isobutylene in the presence of 100 g of the ion exchanger SPC 118, the alkenyl tert-butyl ethers shown in the Table below were obtained analogously to Example 1.

TABLE

| Example | Alkenyl-tert-butyl ether | n | bp. [°C./mbar] | Yield (% of theory) | Fragrance |
|---|---|---|---|---|---|
| 2 | Oct-7-en-1-yl tert-butyl ether | 6 | 53–55/0.6 | 75% | Green, herbaceous, floral (tagetes) |
| 3 | Nona-8-en-1-yl tert-butyl ether | 7 | 110–112/20 | 82% | Dry powdery (tagetes, sage) |
| 4 | Deca-9-en-1-yl tert-butyl ether | 8 | | | |

USE EXAMPLE

A cream perfume of the following composition was prepared using 1-tert-butyoxyhex-5-end:

| | |
|---|---|
| Benzyl isoeugenol | 50 parts by weight |
| Dimethylbenzylcarbinyl acetate | 50 parts by weight |
| Tetrahydrolinalool | 150 parts by weight |
| Tetrahydrolinalyl acetate | 200 parts by weight |
| Citronellyl acetate | 50 parts by weight |
| Phenylacetaldehyde dimethyl acetal | 40 parts by weight |
| Balinol ® (FDO) | 20 parts by weight |
| Phenylethyl alcohol | 90 parts by weight |
| Hedione ® (Firmenich) | 60 parts by weight |
| Lysmeral ® (BASF) | 60 parts by weight |
| Anisaldehyde | 30 parts by weight |
| Geraniol | 80 parts by weight |
| Cedryl acetate | 60 parts by weight |
| Dipropylene glycol | 20 parts by weight |
| 1-tert-butoxyhex-5-ene | 40 parts by weight |
| | 1,000 parts by weight |

The addition of 1-tert-butoxyhex-5-ene gives the composition a pleasantly fresh, somewhat fruity note and the typical tagetes effect. The composition also has greater radiating power.

We claim:

1. A 1-tert-butoxy-ω-alkene of the formula I $$CH_2=CH-(CH_2)_4-C(CH_3)_3 \qquad (I)$$

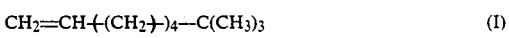

wherein n is an integer of from 4 to 10.

2. A process for imparting fragrance properties to perfumes or to perfumed products, or for improving or modifying the fragrance properties of the said perfumes or products, wherein a 1-tert-butoxy-ω-alkene of the formula I as claimed in claim 1 is added to these products.

3. A scent composition containing a 1-tert-butoxy-ω-alkene of the formula I as claimed in claim 1.

4. A process for imparting fragrance properties to perfumes or to perfumed products, or for improving or modifying the fragrance properties of the said perfumes or products, wherein a 1-tert-butoxy-w-alkene of the formula I $$CH_2=CH-(CH_2-)_nO-C(CH_3)_3 \qquad (I)$$

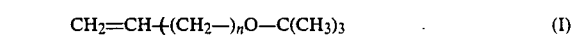

where n is an integer from 4 to 10 is added to these products.

5. A scent composition containing a 1-tert-butoxy-ω-alkene of the formula I $$CH_2=CH(CH_2)_n-C(CH_3)_3 \qquad (I)$$

where n is an integer from 4 to 10.

* * * * *